United States Patent [19]

Endo et al.

[11] Patent Number: 5,245,050

[45] Date of Patent: Sep. 14, 1993

[54] DERIVATIVES OF PHYSIOLOGICALLY ACTIVE SUBSTANCE ML-236B AND PROCESS FOR PRODUCTION THEREOF

[75] Inventors: Akira Endo, Tokyo; Tadashi Toshioka, Urayasu; Isao Umezawa, Tokyo; Masayuki Yuasa, Tokyo; Takashi Inaba, Tokyo; Tsutomu Inoue, Funabashi, all of Japan

[73] Assignee: Tobishi Yakuhin Kogyo Kabushiki Kaisha, Tokyo, Japan

[21] Appl. No.: 427,085

[22] PCT Filed: Feb. 28, 1989

[86] PCT No.: PCT/JP89/00201

§ 371 Date: Oct. 3, 1989

§ 102(e) Date: Oct. 3, 1989

[87] PCT Pub. No.: WO89/08094

PCT Pub. Date: Sep. 8, 1989

[30] Foreign Application Priority Data

Feb. 28, 1988 [JP] Japan .................................. 63-44579

[51] Int. Cl.$^5$ ...................... C07D 309/30; C07C 69/34
[52] U.S. Cl. ...................................... 549/292; 560/194
[58] Field of Search ......................... 549/292; 560/194

[56] References Cited

U.S. PATENT DOCUMENTS 4,137,322 1/1979 Endo et al. ........................... 548/344
4,937,259 6/1990 Lee ...................................... 549/292

FOREIGN PATENT DOCUMENTS 0130548 7/1985 Japan .
0093781 4/1991 Japan .

OTHER PUBLICATIONS

C. H. Kuo et al., J. Org. Chem. 1983, 48, 1991–1998.
Endo, Journal of Antibiotics, 33(3):334–336 (Mar. 1980).

Primary Examiner—C. Warren Ivy
Assistant Examiner—A. A. Owens
Attorney, Agent, or Firm—Ladas & Parry

[57] ABSTRACT

A compound represented by the following general formula:

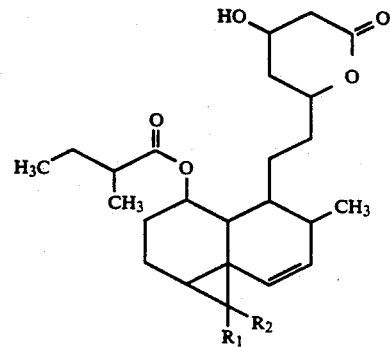

wherein $R_1$ and $R_2$ are the same or different, and represent a hydrogen or halogen, and ring-opened free acid, amides and salts thereof are provided. The present invention also provides a process for the production of the above-mentioned compound starting from the known compound ML-236B.

5 Claims, No Drawings

DERIVATIVES OF PHYSIOLOGICALLY ACTIVE SUBSTANCE ML-236B AND PROCESS FOR PRODUCTION THEREOF

TECHNICAL FIELD

The present invention relates to novel compounds with a three-membered cyclic structure having a cholesterol synthesis inhibitory activity, and processes for the production thereof. According to the present invention, stable, novel compounds can be easily produced.

BACKGROUND ART

In 1971, the present inventors established an efficient method of developing a cholesterol synthesis inhibiting agent aimed at a compound produced by a microorganism, and screening was carried out, and in 1973 found that a compound designated as ML-236B having the desired activity is produced by a microorganism of the genus *Penicillium* (Japanese Examined Patent Publication, Kokoku, No. 56-12114); in 1981 by a microorganism of the genus *Paecilomyces* (Japanese Examined Patent Publication, Kokoku, No. 59-45360; in 1982 by a microorganism of the genus *Hypomyces* (Japanese Examined Patent Publication, Kokoku, No. 62-19158); by a microorganism of the genus *Trichoderma* (Japanese Examined Patent Publication, Kokoku, No. 62-19519; and by a microorganism of the genus *Eupenicillium*. Attention has been paid to compounds belonging to this class as therapeutic agents for arteriosclerosis and coronary heart disease, because these compounds specifically inhibit HMG-CoA reductase and repress the synthesis of cholesterol.

Although, as stated above, the compounds belonging to this class exhibit a specific and notable therapeutic efficacy, they are relatively unstable, and therefore, difficult modification steps are necessary for the production thereof.

DISCLOSURE OF THE INVENTION

On the basis of the above, the present invention relates to useful novel compounds and simple processes for the production thereof. More specifically, the conventional ML-236B compound of microbial origin is heated in the presence of a cyclopropanating agent to saturate a double bond and to form a three-membered cyclic structure, resulting in a remarkably stable compound.

Among the present compounds are those represented by the following general formula:

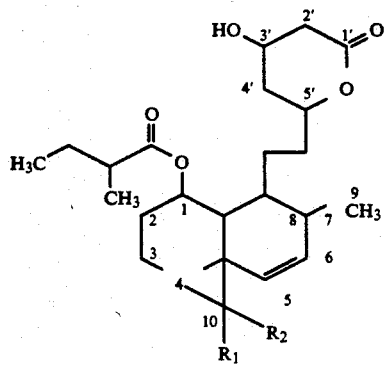

wherein $R_1$ and $R_2$ are the same or different and represent a hydrogen or halogen atom, as well as free acids, amides and salts thereof.

The present compound can be produced by heating the ML-236B compound represented by the following formula:

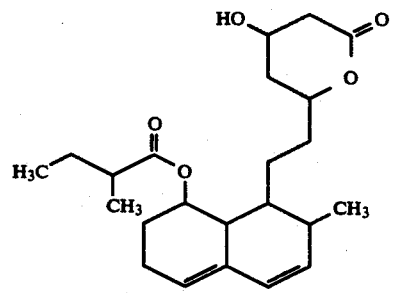

in the presence of a cyclopropanating agent to obtain a halogenated compound containing a three-membered cyclic moiety, and if desired, reducing the halogenated compound partially or totally for dehalogenation. Ring-opened free acids, amides and salts can be easily produced by treating the halogenated compound or dehalogenated compound by an usual base such as ammonia or sodium hydroxide, similar to other compounds belonging to the same class.

BEST MODE OF CARRYING OUT THE INVENTION

According to the present invention, effective cyclopropanating agents include methane derivatives capable of forming carbene, as well as alkaline metal salts of chlorodifluoroacetic acid, dichlorofluoromethane, iodoform, chloroform and bromoform; and effective dehalogenating agents particularly include tributyl tin hydride. As a solvent for the cyclopropanation, diethyleneglycol dimethyl ether (Diglyme), chloroform, and dichloromethane are preferable.

Salts of the present compounds are, for example, salts of alkali metals, such as potassium and sodium; salts of alkali earth metals such as magnesium and calcium; and ammonium salts.

HMG-CoA Reductase Inhibitory Activity

The HMG-CoA reductase activity can be determined by using [$^{14}$C] HMG-CoA as a substrate and measuring the resulting [$^{14}$C] mevalonic acid (Kuroda and Endo, Biochem Biophys Acta, 486, 70–81), as described in detail in the following.

A reaction mixture contains 100 mM of potassium phosphate buffer (pH 7.4), 10 mM of EDTA, 10 mM of dithiothreitol, 10 mM of NADPH, 0.11 mM of DL-[3-$^{14}$C] HMG-CoA (4.5 mCi/mmol), and 0.6 mg/ml of rat liver microsome fraction. The final volume of reaction mixture is 50 μl including 1 μl of a methanol solution of a test sample. A reaction is started by adding the substrate HMG-CoA, continued at 37° C. for 30 minutes, and terminated by adding 10 μl of 2N hydrochloric acid solution To this reaction mixture is added 20 μl of 100 mM [5-$^3$H] mevaronic acid (22.7 μCi/mmol), and the reaction is carried out at 37° C. for a further 15 minutes. Using 40 μl of this reaction mixture as a carrier, 5 μl of 200 mM mevaronic acid (lactone type) is spotted on a silica gel plate, and after development by benzene/acetone (1:1) mixture, a spot of mevaronic acid is peeled off and suspended in a liquid scintillator to measure the radio activity thereof. The inhibitory activity is expressed by an amount of a sample necessary to inhibit the HMG-CoA reductase activity to 50% ($I_{50}$ value).

| Compound number | $I_{50}$ (μg/ml) | Enzyme activity (% relating to control) | | |
|---|---|---|---|---|
| | | 10 μg/ml | 1 μg/ml | 0.1 μg/ml |
| (1) | 0.3 | | 27 | 74 |
| (4) | 0.22 | 7.6 | | 63 |
| (6) | 0.30 | 4.7 | | 71 |
| (7) | >1 | 30 | | 98 |

Next, the present invention is more definitively illustrated by Examples.

EXAMPLE 1

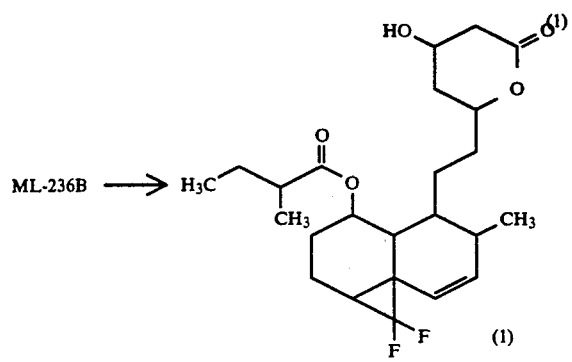

First, 11.0 g of ML-236B and a stirrer were put into a 300 ml three-necked flask, and then 150 ml of Diglyme was added thereto. A titrating funnel containing 100 ml of a solution of 15.0 g of sodium chlorodifluoroacetate in Diglyme and a condenser were attached to this flask, and the reaction mixture was refluxed. During the refluxing, the solution of sodium chlorodifluaroacetate in Diglyme was dropwise added during 1 hour and 20 minutes, and after a further refluxing for 20 minutes, the reaction mixture was allowed to cool. The reaction mixture was then diluted with 500 ml of benzene, and the diluted mixture was successively washed with water and saturated NaCl solution. After the aqueous layer was extracted with 100 ml of benzene, and the benzene layer was washed with water, the benzene layers were combined and dried over anhydrous magnesium sulfate. After filtration of this mixture, the solvent was evaporated under reduced pressure to obtain a crude product which showed two spots on TLC (n-hexane/ ethyl acetate=1:1; silica gel). This crude product was separated on a column (n-hexane/ethyl acetate=3:2; silica gel). The product having a larger Rf value was a compound wherein a hydroxyl group at a 3, position of the lactone site was dehydrated and a double bond was formed at 2'-3' position, and the product having a smaller Rf value was a mixture of ML-236B and the compound (1). The mixture having a smaller Rf value was dissolved in 60 ml of dichloromethane in an eggplant-shaped flask, and reacted with 492 mg of metachloroperbenzoic acid at room temperature for two hours. To the reaction mixture were added 20 ml of saturated sodium bicarbonate aqueous solution and 2 ml of saturated sodium thiosulfate, and after the whole was stirred, a dichloromethane layer was separated by a separatory funnel. An aqueous layer was extracted with 10 ml of dichloromethane, the dichloromethane layers were combined, and successively washed with water and a saturated NaCl solution, dried over anhydrous magnesium sulfate, and filtered to obtain a solution, from which the solvent was then removed under reduced pressure to obtain a residual product. The residual product was then purified on a column chromatography (n-hexane/ethyl acetate=3:2; silica gel) to obtain 4.9 g of the compound (1) as colorless crystal. The melting point was 83.0° C. to 84.0° C.

This product had the same Rf value as that of ML-236B, and did not show a substantial UV absorption at 254 mm.

$^1$H-NMR (CDCl$_3$ δppm): 6.02 (1H, dd, J=9.7, 6.1 Hz), 5.15 (1H, m), 5.14 (1H, d, J=9.7 Hz), 4.65 (1H, m), 4.38 (1H, m), 2.75 (1H, dd, J=17.5, 5.1 Hz), 2.65 (1H, ddd, J=17.5, 4.1, 1.2 Hz), 2.43 (1H, m), 2.36 (1H, qt, J=7.1, 7.1 Hz), 2.05-1.25 (6H, m), 1.12 (3H, d, J=7.1 Hz), 0.91 (3H, d, J=7.6 Hz), 0.89 (3H, t, J=7.1 Hz)

(Signals for hydroxyl group, methylene group at 2'-position, etc., shifted depending on the concentration for measurement.)

$^{13}$C-NMR (CDCl$_3$ δppm): 116.3 ppm, t(J=294.2 Hz: C-F coupling)

First, 100 mg of the product was dissolved in tetrahydrofuran, and reacted with an equivalent of 10N sodium hydroxide to obtain 89 mg of sodium salt of the compound (1). Then 50 mg of the sodium salt of the compound (1) was dissolved in water, and the pH of the solution was adjusted to 3 to obtain 50 mg of a carboxylic acid of the compound (1).

EXAMPLE 2

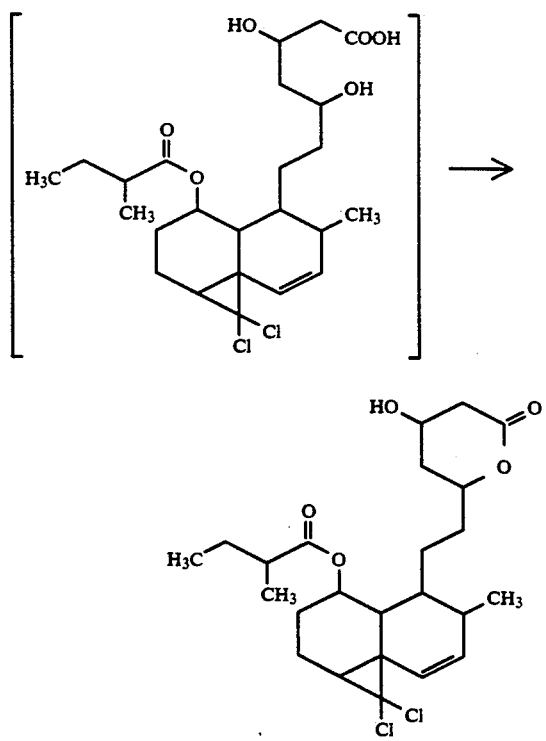

First, 24.8 g of ML-236B and a stirrer were put into a 1 l three-necked flask, and a titration funnel and a condenser were attached to the flask. To this three-necked flask were added 300 ml of chloroform and 4.0 g of trimethylbenzylammonium chloride, and 140 g of 10N sodium hydrochloride was put into the titration funnel. When the sodium hydroxide solution was dropwise added, a vigorous reaction occurred with refluxing. After the heat generation was terminated, the reaction mixture was heated to reflux for 30 minutes on an oil bath, and then cooled on ice water. The reaction mixture was adjusted with concentrated hydrochloric acid to pH 3 under stirring. This solution was transferred to a separatory funnel, a chloroform layer was removed, and an aqueous layer was twice extracted with 100 ml of chloroform. The chloroform layers were combined, twice washed with saturated NaCl solution, and dried over anhydrous magnesium sulfate. After filtration of the mixture, the filtrate was concentrated to obtain a residual product (intermediate crude product). The product was dissolved in 300 ml of ethyl acetate, and a stirrer was put into the solution, to which 30 ml of a mixture of 5% hydrochloric acid and ethyl acetate was then added, and the whole was stirred for 30 minutes. 200 ml of saturated sodium bicarbonate was added to the mixture to make it alkaline, and the mixture was transferred to a separatory funnel to separated an ethyl acetate layer. An aqueous layer was extracted twice with 100 ml of ethyl acetate, and the separated ethyl acetate layers were combined with the previously separated ethyl acetate. The combined ethyl acetate layer was washed twice with water and twice with saturated NaCl solution, and dried over anhydrous magnesium sulfate. After filtration, the filtrate was concentrated to obtain a crude product of compound (2). This product was applied to a column (n-hexane/ethyl acetate=3:2 ; silica gel) to separate a fraction which exhibited the same Rf value as that of ML-236B and a very weak UV absorption, and 17.5 g of a colorless amorphous solid was obtained.

$^1$H-NMR (CDCl$_3$ δppm): 6.19 (1H, dd, J=9.5, 6.4 Hz), 5.25 (1H, d, J=9.5 Hz), 5.15 (1H, m), 4.67 (1H, m), 4.38 (1H, m), 2.74 (1H, dd, J=17.6, 5.1 Hz), 2.63 (1H, ddd, J=17.6, 4.1, 1.2 Hz), 2.44 (1H, m), 2.23 (1H, qt, J=7.1, 7.1 Hz), 2.05 - 1.2 (14H, m), 1.10 (3H, d, J=7.1 Hz), 0.94 (3H, d, J=7.1 Hz), 0.88 (3H, t, J=7.1 Hz)

(Signals for hydroxyl group, methylene group at 240-position, etc., shifted depending on the concentration for measurement.)

This product was treated in the same manner as in Example 1 to obtain sodium salt as amorphous solid.

The intermediate crude product in this Example was purified on a column (1% methanol/chloroform; silica gel) to obtain 78 mg of the intermediate product in purified form.

EXAMPLE 3

ML-236B ⟶ (3)

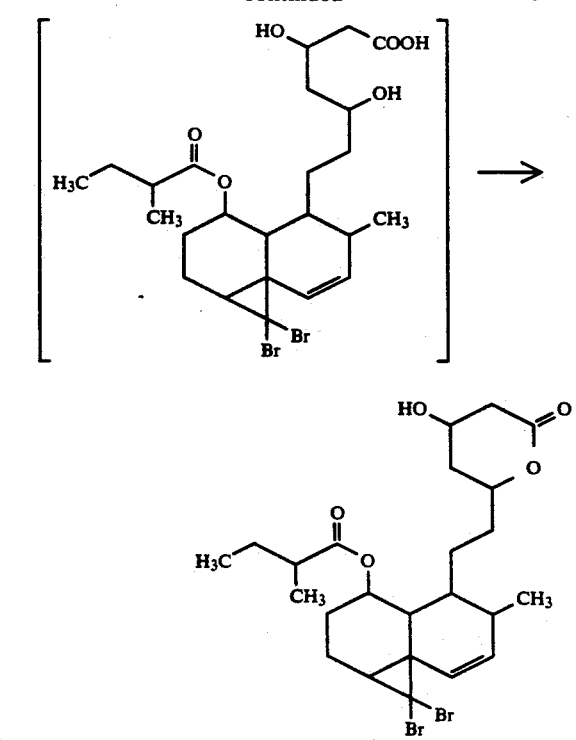

First, 10.0 g of ML-236B and a stirrer were put into a 500 ml three-necked flask, and a titration funnel and a condenser were attacked to the flask. Then 50 ml of methylene chloride was added to the three-necked flask to dissolve the ML-236B, and 70 g of a 10N sodium hydroxide aqueous solution was added at once. Then 50 g of bromoform was put into the titration funnel, 4.0 g of trimethyl benzylammonium chloride was put into the three-necked flask, and the mixture was heated to reflux on an oil bath. While refluxing, the bromoform was dropwise added for about 20 minutes, resulting in a vigorous reaction. After finishing the addition, the mixture was refluxed for 60 minutes at the same temperature, and then cooled on ice water. After an adjustment to pH 3 with concentrated hydrochloric acid, 100 ml of chloroform was added to the mixture, which was then transferred to a separatoly funnel to separate a chloroform layer. An aqueous layer was extracted with 50 ml of chloroform, and the chloroform layer was separated and combined with the previously separated chloroform layer. The combined chloroform layer was washed twice with a saturated NaCl solution, and dried over anhydrous magnesium sulfate. After filtration, the solvent was evaporated to obtain a residual matter (intermediate crude product). To the thus-obtained residue were added 100 ml of ethyl acetate, 10 ml of 5% hydrochloric acid/ethyl acetate and a stirrer, and reaction was carried out at room temperature for 30 minutes. The reaction mixture was washed with 100 ml of a saturated sodium bicarbonate aqueous solution, and after separation, the aqueous layer was extracted with 50 ml of ethyl acetate. The ethyl acetate layers were combined, dried over anhydrous magnesium sulfate, and filtrated to obtain a filtrate, from which the solvent was then evaporated to obtain a residue. The thus obtained residue was applied to a column (n-hexanel ethyl acetate=3:2; silica gel) to obtain 12.0 g of the desired compound having the same Rf value as that of ML-236B and showing an UV absorption, as colorless amorphous solid.

¹H-NMR (CDCl₃ δppm): 6.23 (1H, dd, J=9.3, 6.3 Hz), 5.31 (1H, d, J=9.3 Hz), 5.14 (1H, m), 4.65 (1H, m), 4.37 (1H, m), 2.74 (1H, dd, J=17.5, 4.9 Hz), 2.63 (1H, ddd, J=17.5, 4.1, 1.2 Hz), 2.42 (1H, m), 2.32 (1H, qt, J=6.9, 6.9 Hz), 2.05 - 1.22 (16H, m), 1.09 (3H, d, J=6.8 Hz), 0.96 (3H, d, J=6.9 Hz), 0.88 (3H, t, J=7.3 Hz)

(Signals for hydroxyl group, methylene group at 2'-position, etc., shifted depending on the concentration for measurement.)

EXAMPLE 4

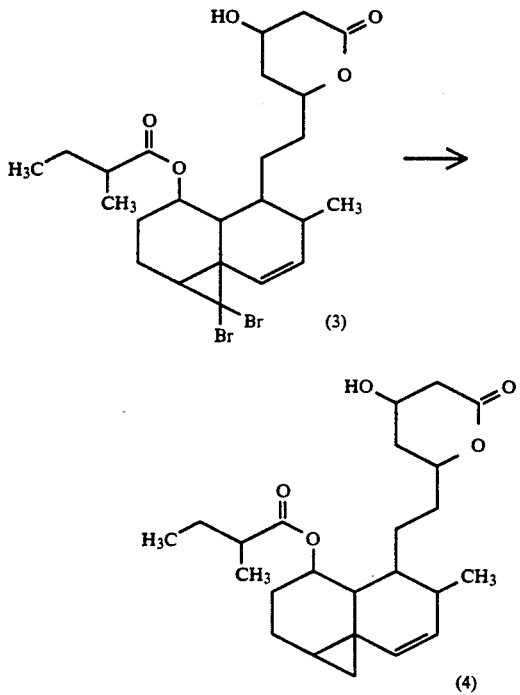

First, 30.0 g of ML-236B, 11.0 g of trimethylbenzylammonium chloride, a stirrer, 200 ml of methylene chloride, and 200 ml of 7.5N sodium hydroxide were put into a 1 l three-necked flask, and a condenser and a titration funnel containing 150 g of bromoform were attached to the flask. The mixture was heated to reflux in an oil bath and the bromoform was dropwise added while vigorously stirring. After the addition, the mixture was refluxed for one hour at the same temperature, and then cooled on ice water. Concentrated hydrochloric acid was gradually added to the reaction mixture to adjust pH 3, at low temperature under stirring. The mixture was transferred to a separatory funnel, and shaken with 100 ml of chloroform and 200 ml of saturated NaCl solution. An organic layer was separated, and an aqueous layer was extracted with 100 ml of chloroform. The organic layers were combined, washed twice with saturated NaCl solution, and dried with anhydrous magnesium sulfate. After filtration, the solvent was evaporated to obtain a residue. The residue was dissolved in 400 ml of ethyl acetate, and to the solution was added, at once, 90 ml of 5% hydrochloric acid/ethyl acetate under stirring, followed by a further stirring for 30 minutes. To this mixture was gradually added 300 ml of saturated sodium bicarbonate aqueous solution, and after stirring, an ethyl acetate layer was separated and an aqueous layer was extracted with 100 ml of ethyl acetate. The ethyl acetate layers were combined, successively washed with water and saturated NaCl solution, and dried over anhydrous magnesium sulfate. After filtration, the solvent was evaporated to obtain a residue. The residue was applied to a column (n-hexane/ethyl acetate=2:1: silica gel), and after a separation of unreacted bromoform, the eluate was changed to n-hexanel/ethyl acetate=1:2 to elute a fraction containing the compound (3). The solvent was removed, and the resulting residue was dissolved in 500 ml of benzene in a 1 l eggplant-shaped flask. A condenser was attached to the flask, and nitrogen gas made to flow therethrough. To the reaction mixture were added 62.0 g of tri-n-butyl tin hydride and 2.0 g of azobisisobutyronitrile under nitrogen atmosphere, and the mixture was heated to reflux for one hour. After cooling, the reaction mixture was applied to a column (n-hexane/ethyl acetate=2:1; silica gel), the tin compound was eliminated, and the eluate was changed to n-hexane/ethyl acetate=1:2 to separate a fraction having the same Rf value as that of ML-236B and showing a weak UV absorption. After the solvent was evaporated, the residue was applied to a column (n-hexane/ethyl acetate=1:1; silica gel) to repurify the product. After fractionation, the solvent was evaporated to obtain a residue. To the residue was added n-hexane, which was then completely evaporated to obtain 20.0 g of the desired compound as colorless amorphous solid.

¹H-NMR (CDCl₃ δppm): 5.78 (1H, dd, J=9.5, 6.3 Hz), 5.05 (1H, m), 4.86 (1H, d, J=9.5 Hz), 4.62 (1H, m), 4.37 (1H, m), 2.74 (1H, dd, J=17.4, 5.1 Hz), 2.61 (1H, ddd, J=17.1, 4.1, 1.2 Hz), 2.39 (1H, qt, J=6.9, 6.9 Hz), 2.32 (1H, m), 2.08 (1H, brs), 2.02-1.05 (14H, m), 1.14 (3H, d, J=6.9 Hz), 0.92 (3H, d, J=7.8 Hz), 0.90 (3H, t, J=7.4 Hz), about 0.9 (1H, m), 0.62 (1H, dd, J=9.3, 4.4 Hz), 0.49 (1H, dd, J=6.3, 4.4 Hz)

(Signals for hydroxyl group, methylene group at 2'-position, etc., shifted depending on the concentration for measurement.)

EXAMPLE 5

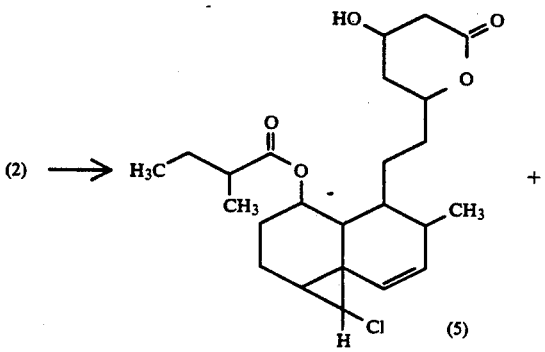

-continued

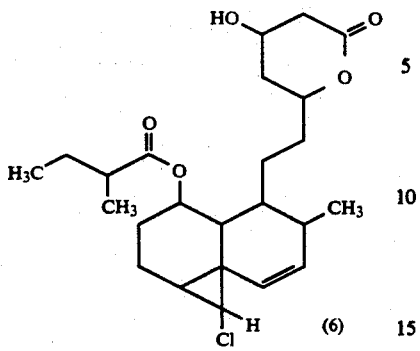

EXAMPLE 6

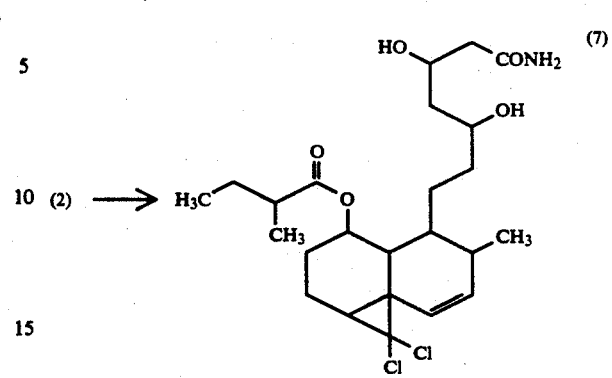

First, 2.74 g of the compound (2), a stirrer and 50 ml of benzene were put into a 100 ml three-necked flaske and a condenser was attached to the flask, which was then purged with nitrogen. Then 3.43 ml of tri-n-butyl tin hydride and 100 mg of azobisisobutyronitrile were added to the flask in nitrogen atmosphere, and the reaction mixture was heated to reflux on an oil bath. After cooling, the reaction mixture was applied to a column (n-hexane/ethyl acetate=2:1; silica gel), the tin compound was separated, and the eluate was changed to n-hexane/ethyl acetate=1:2 to provide a mixture of two compounds having similar Rf values. This mixture was separated by a column (n-hexane/ethyl acetate=1:1; silica gel), and 760 mg each of the compound (5) as colorless amorphous solid and compound (6) as a colorless amorphous solid were obtained.

Compound (5)

$^1$H-NMR (CDCl$_3$ δppm): 5.88(1H, dd, J=9.5, 6.1 Hz), 5.17 (1H, m), 4.9 (1H, d, J=9.5 Hz), 4.62 (1H, m), 4.37 (1H, m), 3.08 (1H, d, 7.8 Hz), 2.74 (1H, dd, J=17.6, 4.9 Hz), 2.62 (1H, ddd, J=17.6, 4.1, 1.2 Hz), 2.40 (1H, m), 2.37 (1H, brs), 2.35 (1H, qt, J=7.1, 7.1 Hz), 2.05 - 1.20 (15H, m), 1.12 (3H, d, J=7.1 Hz), 0.91 (3H, d, J=7.1 Hz), 0.89 (3H, t, J=7.3 Hz)

(Signals for hydroxyl group, methylene group at 2'-position, etc., shifted depending on the concentration for measurement.)

Compound (6)

$^1$H-NMR(CDCl$_3$ δppm): 6.12 (1H, dd, J=9.5, 6.4 Hz), 5.22 (1H, d, J=9.5 Hz), 5.07 (1H, m) 4.63 (1H, m), 4.37 (1H, m), 2.95 (1H, d, J=4.9 Hz), 2.76 (1H, dd, J=17.5, 5.1 Hz), 2.62 (1H, ddd, J=17.5, 4.0, 1.2Hz), 2.40 (1H, m) 2.37 (1H, qt, J=7.1, 7.1 Hz), 2.10 (1H, brs), 2.03 - 1.20 (15H, m), 1.13 (3H, d, J=7.1 Hz), 0.95 (3H, d, J=7.3 Hz), 0.89 (3H, t, J=7.6Hz)

(Signals for hydroxyl group, methylene group at 2'-position, etc., shifted depending on the concentration for measurement.)

First, 3.60 g of the compound (2) was dissolved in 30 ml of ethyl ether in a 100 ml of three-necked flask, and a stirrer was put into the flask, which was then purged with nitrogen. The outside of the flask was cooled with dry ice/acetone, and ammonia gas was introduced itto the flask to add about 100 ml of ammonia. After a reaction at 33° C. for 40 minutes, the reaction mixture was warmed with water to 0° C. The reaction mixture was then diluted with 100 ml of ethyl acetate and washed with water. Am aqueous layer was separated and extracted with 50 ml of ethyl acetate, and after separation, the ethyl acetate was combined with the previously separated ethyl acetate layer. The ethyl acetate layer was washed twice with saturated NaCl solution, and dried over an hydrous magnesium sulfate. After filtration, the solvent was evaporated to obtain a mixture of two components, one of which showed the same Rf value as that of the starting material and the other showed an Rf value smaller than that of the starting material. This mixture was separated by a column (n-hexane/ethyl acetate=1:2, silica gel) to obtain 540 mg of ML-236B, and 3.16 g of the compound (7) as colorless amorphous solid.

$^1$H-NMR (CDCl$_3$ δppm): 6.47 (1H, brs), 6.26 (1H, dd, J=9.5, 6.9 Hz), 5.68 (1H, brs), 5.24 (1H, m), 5.22 (1H, d, J=19.5 Hz), 4.24 (1H, m), 3.82 (1H, m), 2.40 (2H, d, J=6.3 Hz), 2.35 (1H, qt, J=7.1, 7.1 Hz), 2.33 (1H, m), 2.00 - 1.15 (17H, m), 1.11 (3H, d, J=7.1 Hz), 0.91 (3H, d, J=7.1 Hz), 0.89 (3H, t, J=7.3 Hz)

(Signals for amine and hydroxyl group shift depending on the concentration for measurement.)

EXAMPLE 7

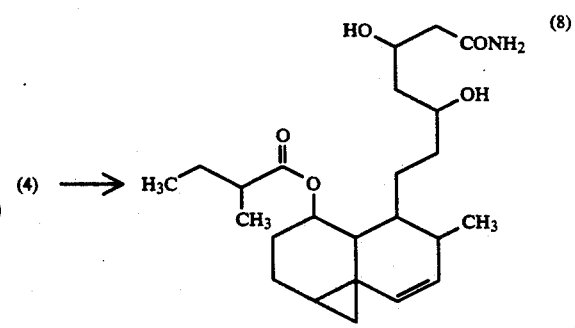

First, 2.4 g of the compound (4) was treated according to the same procedure as in Example 6 to obtain 2.11 g of the desired compound (8) as colorless amorphous solid. Further, ammonia gas was introduced into a solution of 1.20 g of the compound (4) in methanol, followed by a further treatment as described above to obtain 480 mg of the compound (8) and 590 mg of methyl ester thereof.

Compound (8)

$^1$H-NMR (CDCl$_3$ δppm): 6.50 (1H, brs), 5.79 (1H, dd, J=9.5, 6.5 Hz), 5.78 (1H, brs), 5.12 (1H, m), 4.88 (1H, d, J=9.5 Hz), 4.80 (1H, brs), 4.24 (1H, m), 3.80 (1H, m), 3.76 (1H, brs), 2.40 (1H, qt, J=7.1, 7.1 Hz), 2.39 (1H, d, J=6.3 Hz), 2.30 (1H, m), 2.12 - 1.00 (15H, m), 1.14 (3H, d, J=7.1 Hz), 0.90 (3H, d, J=7.2 Hz), 0.90 (3H, t, J=7.5 Hz), 0.63 (1H, dd, J=9.2, 4.4 Hz), 0.47 (1H, dd, J=6.3, 4.4 Hz).

INDUSTRIAL APPLICABILITY

The novel compounds of the present invention specifically inhibit HMG-CoA reductase and repress the biosynthesis of cholesterol, and therefore, are promising as an effective drug compound for therapeutic agents for arteriosclerosis and coronary heart disease.

We claim:

1. A compound represented by the formula:

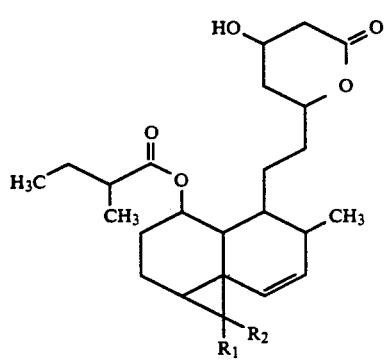

wherein $R_1$ and $R_2$ are the same or different, and represent a hydrogen or halogen atom, and ring-opened free acid, amides and salts thereof.

2. A process of production of a compound represented by the formula:

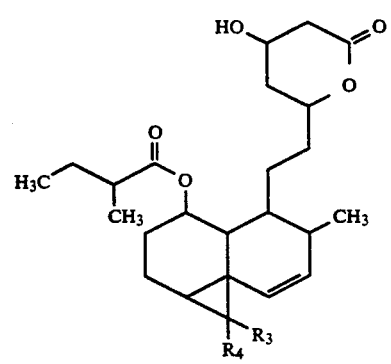

wherein $R_3$ and $R_4$ are the same or different, and represent a halogen atom, and ring-opened free acid, amides and salts thereof, comprising reacting ML-236B compound represented by the formula:

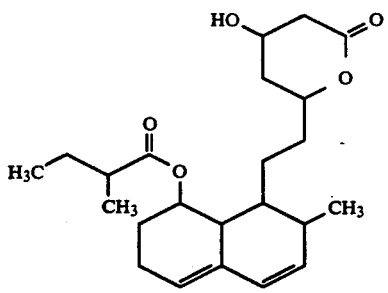

with a cyclopropanating agent, and if desired treating the product with a base.

3. A process for production of a compound represented by the formula:

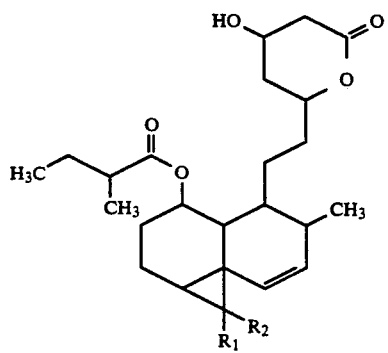

wherein $R_1$ and $R_2$ are the same or different represent a hydrogen or halogen atom with a proviso that both $R_1$ and $R_2$ are not simultaneously halogen atoms, and ring-opened free acid, amides and salts thereof, comprising treating a compound represented by the formula:

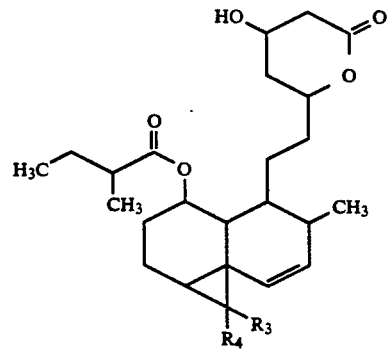

wherein $R_3$ and $R_4$ are the same or different halogen atoms, with a reducing agent, and if desired treating with a base.

4. A process for production of a compound represented by the formula:

wherein $R_1$ and $R_2$ are the same or different, and represent a hydrogen or halogen atom, and salts and amides thereof, comprising treating a compound represented by the formula:

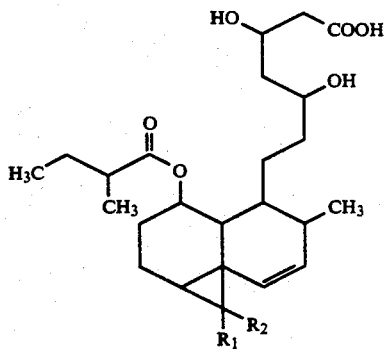

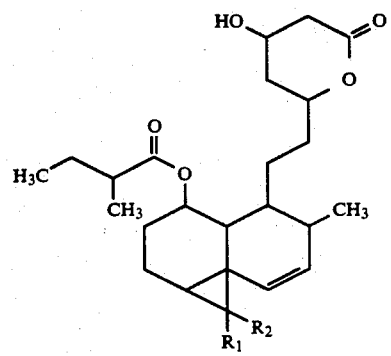

wherein $R_1$ and $R_2$ are the same or different, and represent a hydrogen or halogen atoms, with a base.

5. A process for production of a compound represented by the formula:

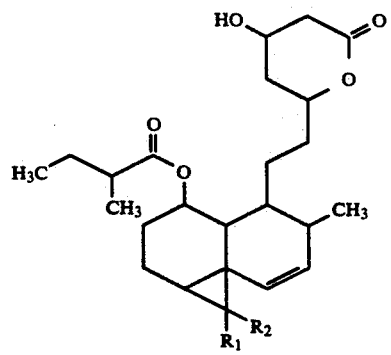

wherein $R_1$ and $R_2$ are the same or different, and represent a hydrogen or halogen atom, with a proviso that both $R_1$ and $R_2$ are not simultaneously halogen atoms, and ring-opened free acid, amides and salts thereof, comprising reacting a ML-236B compound represented by the formula:

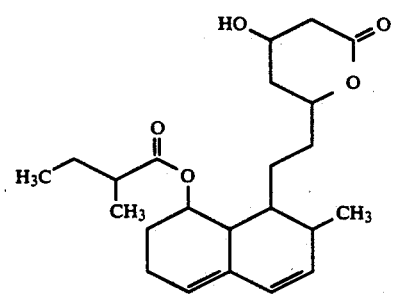

with a cyclopropanating agent, treating a resulting compound with a reducing agent, and if desired, treating a resulting compound with a base.

* * * * *